(12) United States Patent
Lee

(10) Patent No.: US 9,642,870 B2
(45) Date of Patent: May 9, 2017

(54) COMPOSITION FOR PREVENTING OR ALLEVIATING ATOPIC DERMATITIS COMPRISING IMMUNOSUPPRESSANT AND TRANSGLUTAMINASE 2 INHIBITOR

(71) Applicant: Dongguk University Industry-Academic Cooperation Foundation, Seoul (KR)

(72) Inventor: Ai-Young Lee, Jongno-gu Seoul (KR)

(73) Assignee: Dongguk University Industry-Academic Cooperation Foundation, Seoul (KR)

( * ) Notice: Subject to any disclaimer, the term of this patent is extended or adjusted under 35 U.S.C. 154(b) by 70 days.

(21) Appl. No.: 14/360,104

(22) PCT Filed: Nov. 20, 2012

(86) PCT No.: PCT/KR2012/009842
§ 371 (c)(1),
(2) Date: May 22, 2014

(87) PCT Pub. No.: WO2013/077617
PCT Pub. Date: May 30, 2013

(65) Prior Publication Data
US 2015/0231161 A1    Aug. 20, 2015

(30) Foreign Application Priority Data
Nov. 22, 2011  (KR) .................. 10-2011-0122447

(51) Int. Cl.
  A61K 31/7008   (2006.01)
  A61K 45/00     (2006.01)
  A61K 38/13     (2006.01)
  A61K 31/436    (2006.01)
  A61K 45/06     (2006.01)

(52) U.S. Cl.
  CPC ........ *A61K 31/7008* (2013.01); *A61K 31/436* (2013.01); *A61K 38/13* (2013.01); *A61K 45/06* (2013.01)

(58) Field of Classification Search
None
See application file for complete search history.

(56) References Cited

FOREIGN PATENT DOCUMENTS

| | | |
|---|---|---|
| JP | 2010-518130 | 5/2010 |
| KR | 10-1993-0702014 | 9/1993 |
| KR | 1020080017487 A | 2/2008 |
| KR | 10-2008-0035997 | 4/2008 |
| KR | 10-2010-0017998 | 2/2010 |
| KR | 10-0969634 | 7/2010 |
| KR | 10-2010-099849 | 9/2010 |
| WO | 2008/048076 | 4/2008 |

OTHER PUBLICATIONS

Kim et al. (2012), Scandinavian Journal of Immunology, vol. 75, pp. 471-478.*
KR20100099849 (2010), p. 1-8.*
Rudikoff et al., "Atopic dermatitis," *Lancet*, 1998, 351:1715-21.
Larsen et al., "Epidemiology of Atopic Dermatitis," *Immunology and Allergy Clinics of North America*, 2002, 22(1):1-24.
Leung et al., "Atopic dermatitis," *Lancet*, 2003, 361:151-160.
Yetman et al., "Diagnosis and Management of Atopic Dermatitis," *J. Pediatr Health Care*, 2002, 16:143-145.
Folk et al., "[46] Transglutaminases," *Methods in Enzymology*, 1985, 113:358-375.
Haroon et al., "Tissue transglutaminase is expressed, active, and directly involved in rat dermal wound healing and angiogenesis," *FASEB J.*, 1999, 13:1787-1795.
Kim et al., "Transglutaminases in disease," *Neurochemistry International*, 2002, 40:85-103.
"Severity Scoring of Atopic Dermatitis: The SCORAD Index—Consensus Report of the European Task Force on Atopic Dermatitis," *Dermatology*, 1993, 186:23-31.
Kunz et al., "Clinical Validation and Guidelines for the SCORAD Index: Consensus Report of the European Task Force on Atopic Dermatitis," *Dermatology*, 1997, 195:10-19.
International Search Report for PCT/KR2012/009842 dated Feb. 28, 2013.

* cited by examiner

*Primary Examiner* — Christine J Saoud
*Assistant Examiner* — Jegatheesan Seharaseyon
(74) *Attorney, Agent, or Firm* — Riverside Law LLP

(57) ABSTRACT

The present invention relates to a composition for preventing, treating or alleviating atopic dermatitis comprising an immunosuppressant and a transglutaminase 2 inhibitor as active ingredients. Conjoint administration of an immunosuppressant and a transglutaminase 2 inhibitor according to the present invention makes it possible to achieve far better therapeutic effects than with administration of either an immunosuppressant or a transglutaminase 2 inhibitor alone, since there is a reduction in the dose of an immunosuppressant which is difficult to administer for a long time because of side effects and with which, when discontinued, lesions are liable to become exacerbated to the original state, and since an immunosuppressant is mixed with a transglutaminase 2 inhibitor which in some patients has a lackluster effect in treating atopic dermatitis.

1 Claim, 14 Drawing Sheets

FIG. 9

| Group | | IL-4 | IL-5 | IL-13 | Eotaxin | TARC | TSLP |
|---|---|---|---|---|---|---|---|
| Untreated | | 122.1±25 | 76.4±12.9 | 344.5±61.8 | 276.7±11.5 | 132.6±10.6 | 23.1±1.8 |
| CsA | 2 | 98.5±4.1 | 74.6±5.1 | 353.8±50.9 | 291.2±12.7 | 113.2±10.9 | 20.2±1.5 |
| | 5 | 103.3±8.8 | 79.5±3.9 | 392.1±29.6 | 283.9±6.9 | 125.8±6.9 | 21.3±1.1 |
| | 10 | 105.8±9.6 | 83.6±7.8 | 345.9±17.5 | 261.1±9.4 | 115.9±15.1 | 19.9±0.6 |
| Glu (500) | | 115.5±7.3 | 78.5±3.1 | 385.9±23.3 | 266.6±17.4 | 110.7±17.1 | 19.2±3.4 |
| CsA + Glu (500) | 2 | 64.2±2.3** | 42.2±8.2** | 277.2±11.7** | 214.7±17.4* | 84.2±8.8* | 13.5±2.6* |
| | 5 | 57.9±2.6** | 47.1±2.9** | 203.6±12.6** | 219.2±16.7* | 83.1±5.5* | 14.7±1.6* |
| | 10 | 54.6±2.8** | 40.3±1.4** | 198.2±11.9** | 218.1±15.3* | 90.6±5.4* | 13.2±1.1* |

CsA: cyclosporine A  
Unit of cytokines/chemokines: pg/ml  
** $p<0.01$  
Glu: glucosamine  
Unit of CsA or Glu: mg/kg  
* $p<0.05$

COMPOSITION FOR PREVENTING OR ALLEVIATING ATOPIC DERMATITIS COMPRISING IMMUNOSUPPRESSANT AND TRANSGLUTAMINASE 2 INHIBITOR

STATEMENT REGARDING GOVERNMENT RIGHTS

This invention was made with government support under of the Republic of Korea under Contract No. 1345159869 awarded by Korean Ministry of Science. The government has certain rights in the invention.

CROSS-REFERENCE TO RELATED APPLICATIONS

This application is the U.S. national phase application filed under 35 U.S.C. §371 claiming benefit to International Patent Application No. PCT/KR2012/009842, filed on Nov. 20, 2012, which is entitled to priority under 35 U.S.C. §119(a)-(d) to Korea application no. 10-2011-0122447, filed Nov. 22, 2011, each of which application is hereby incorporated herein by reference in its entirety.

TECHNICAL FIELD

The present invention relates to a composition for preventing, treating or alleviating atopic dermatitis including an immunosuppressant and a transglutaminase 2 inhibitor as active ingredients.

BACKGROUND ART

Atopic dermatitis is an abnormal syndrome of the skin which generally exhibits unknown severe pruritus and is also complexly accompanied with xeroderma, erythema and inflammation on the skin (Lancet. 1998; 351:1715-1721). Atopic dermatitis is a chronic disease causing great inconvenience to the patients' long-term lives, and commonly affects infants or young children. This disease affects 10 to 15% of infants and young children. Looking at the occurrence of atopic dermatitis in a group of atopic dermatitis patients, 60% of the atopic dermatitis occurs in infants aged one or less, and 85% of the atopic dermatitis occurs in young children aged five or less (Lancet. 1998; 351:1715-1721). 40% of child patients suffering from atopic dermatitis improve with age, but the incidence of atopic dermatitis in adults has also increased to approximately 1 to 3% of all adults due to air pollution, environmental pollution and the like caused by sudden industrialization (Immunol. Allergy. Cli. North Am. 2002; 22:1-24), which is two or three times that prior to industrialization (Lancet. 2003; 361:151-160). For this reason, many researchers have been interested in alleviating the clinical symptoms of atopic dermatitis.

The clinical symptoms of atopic dermatitis differ according to individuals. However, atopic dermatitis patients have some representative symptoms: the first being severe itching, the second displeasure due to the patient's skin remaining dry, and the third loss of defense functions in the skin surface due to the dry skin, which facilitates easy penetration of stimulants from the outside and causes an inflammatory response due to rejection of the stimulants by the skin (Lancet. 1998; 351:1715-1721; J. Pediatr. Health Care. 2002; 16; 143-145).

Many studies on the causes and treatment of atopic dermatitis have been conducted so far. However, exact causes and effective treatment of atopic dermatitis have not been clearly established due to the complexity of atopic dermatitis and conflicting data.

Steroids, local anti-inflammatory preparations such as tacrolimus and pimecrolimus, anti-histamine agents, and immunosuppressants such as cyclosporine have are therapeutic agents developed so far that are used to treat atopic dermatitis. Also, photochemotherapy using a hypoallergenic humectant and ultraviolet A has been used clinically as adjuvant therapy. However, such therapy or therapeutic agents are not a basic cure but merely aid in regulating a proper level of symptoms, and have not yet completely satisfied the demands of atopic dermatitis patients.

To meet such demands, the present inventors developed a therapeutic agent for treating atopic dermatitis including glucosamine as an active ingredient, wherein the glucosamine is a natural substance that is a commercially available transglutaminase inhibitor whose safety has been already approved (Korean Patent Publication No. 2008-0035997). However, glucosamine has a therapeutic effect only on some individual patients, and its therapeutic effect is poor on severe atopic dermatitis patients. Meanwhile, immunosuppressants such as cyclosporine have been used for severe atopic dermatitis patients that are resistant to conventional therapeutic methods. Such immunosuppressants exhibit excellent effects, but have problems regarding side effects such as nephrotoxicity, gingival hyperplasia, hypertrichosis, neurotoxicity, hypertension, hyperlipidemia, glycosemia, hyperkalaemia, hyperuricemia, hemolytic uremic syndromes, and infections. Further, although it is difficult to administer an immunosuppressant for a long period of time due to its side effects, the atopic dermatitis returns to its original severe state when administration of the immunosuppressant is discontinued.

DISCLOSURE

Technical Problem

The present inventors have made great efforts to develop a therapeutic method capable of solving the above problems, reducing side effects of immunosuppressants which can induce side effects upon excessive administration and also exhibiting a high therapeutic effect on atopic dermatitis, and found that inclusion of a transglutaminase 2 inhibitor causes a decrease in dose of the immunosuppressant used and an increase in therapeutic effect on atopic dermatitis compared to when the immunosuppressant is administered alone. Therefore, the present invention has been completed based on these facts.

The present invention is designed to solve the problems of the prior art, and therefore it is an object of the present invention to provide a pharmaceutical composition for treating atopic dermatitis and a cosmetic composition for alleviating atopic dermatitis, both of which include an immunosuppressant and a transglutaminase 2 inhibitor as active ingredients, and thus are able to exhibit a superior therapeutic effect of the immunosuppressant even when the immunosuppressant is administered at a reduced dose.

Technical Solution

To solve the above problem of the prior art, according to an aspect of the present invention, there is provided a pharmaceutical composition for preventing or treating atopic dermatitis, which includes an immunosuppressant and a transglutaminase 2 inhibitor as active ingredients.

According to another aspect of the present invention, there is provided a cosmetic composition for alleviating atopic dermatitis, which includes an immunosuppressant and a transglutaminase 2 inhibitor as active ingredients.

Advantageous Effects

Combined administration of the immunosuppressant and the transglutaminase 2 inhibitor according to the present invention can result in a decrease in dose of the immunosuppressant which cannot be continuously administered for a long period of time due to side effects and discontinuance of which rapidly exacerbates lesions into original conditions, and can achieve very excellent effects of treating or alleviating atopic dermatitis, compared to when the immunosuppressant or the transglutaminase 2 inhibitor is administered alone.

DESCRIPTION OF DRAWINGS

FIG. 9 is a diagram showing the results obtained by comparing reduction effects on IL-5, IL-13, eotaxin, TARC and TSLP after cyclosporine (CsA) (2, 5, and 10 mg/kg/day) and glucosamine (500 mg/kg/day) are administered alone or in combination.

BEST MODE

Figure 1:
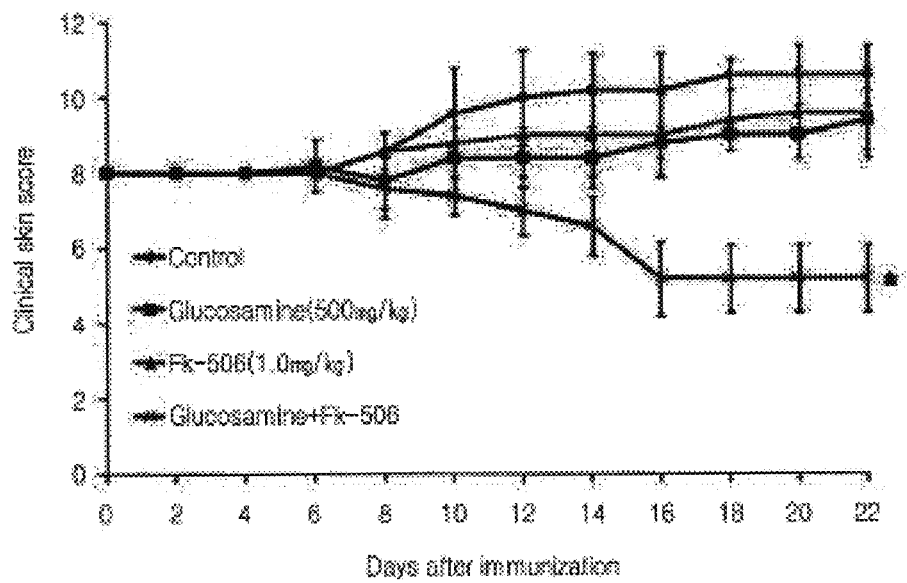
FIG. 1 is a diagram showing the results obtained by measuring and comparing clinical skin scores after glucosamine (500 mg/kg/day) and tacrolimus (FK-506) (1.0 mg/kg/day) are administered alone or in combination.

The present invention is directed to a composition for preventing, treating or alleviating atopic dermatitis, which includes an immunosuppressant and a transglutaminase 2 inhibitor as active ingredients.

The composition includes a pharmaceutical composition and a cosmetic composition.

Hereinafter, the present invention will be described in further detail.

When an immunosuppressant and a transglutaminase 2 inhibitor according to the present invention are administered in combination, secretion of inflammatory cytokines in atopic dermatitis patients may be effectively reduced, and a therapeutic effect on atopic dermatitis may be ensured even when the immunosuppressant is administered at a dose much lower than an effective amount to treat atopic dermatitis, thereby reducing side effects caused by the immunosuppressant.

The term "immunosuppressant" commonly refers to a drug for suppressing an immune response in a living body. Examples of immunosuppressants may include calcineurin inhibitors including glucocorticoid, cyclosporine, tacrolimus (FK506), pimecrolimus, and ISA(TX)247, rapamycin, a Type IV PDE inhibitor, mycophenolate mofetil, dexamethasone, and the like, but the present invention is not limited thereto. For example, all kinds of known immunosuppressants may be used herein.

Also, one immunosuppressant may be used alone, or two or more immunosuppressants may be used in combination. Preferably, at least one selected from the group consisting of cyclosporine, tacrolimus, dexamethasone, and pimecrolimus may be used as the immunosuppressant.

The term "transglutaminase 2 (hereinafter referred to as "TG2") inhibitor" encompasses both of TG2 activator inhibitors or TG2 expression inhibitors. TG2 is an enzyme that catalyzes binding of a glutamine residue and a lysine residue of different proteins to epsilon-gamma-glutamyl lysine (ε-γ-glutamyl lysine) (Methods in Enzymol. 1985; 113: 358-375), and thus has been considered an important factor used to prevent skin damage and heal damaged tissues (FASEB J. 1999; 13: 1787-1795). However, abnormally activated TG2 contributes to the outbreak of various diseases such as brain diseases, arteriosclerosis, inflammatory diseases, autoimmune diseases and fibrosis (Neurochem. Int. 2002; 40: 85-103).

In the present invention, a TG2 activator inhibitor may preferably be an anti-TG2 antibody that can neutralize the activities of TG2. In the present invention, the anti-TG2 antibody may be a polyclonal antibody, or a monoclonal antibody. The antibody according to the present invention may be prepared using conventional methods widely known in the field of immunology using a TG2 protein as an antigen.

Another TG2 activator inhibitor is a compound for suppressing the activities of TG2, and may, for example, include cystamine, putrescine, monodansylcadaverine, w-dibenzylaminoalkylamine, 3-halo-4,5-dihydroisoxazole, a 2-[(2-oxopropyl)thio]imidazolium derivative, and the like. Also, epigallocatechin gallate, or chlorogenic acid may also be used herein.

"Inhibition of expression of a TG2 gene" according to the present invention encompasses inhibition of transcription of a gene and inhibition of translation into a protein, and includes a reduction in expression as well as complete termination of expression of a gene. As a method of inhibition expression of a gene, it is most general to use antisense molecules. The functions of the antisense molecules in inhibiting expression of a target gene include inhibition of transcription initiation by formation of triple chains, inhibition of transcription by hybridization at a site in which a local open loop architecture is formed by an RNA polymerase, inhibition of transcription by hybridization at RNA which is being synthesized, splicing inhibition by hybridization at the junction of intron and exon, splicing inhibition by hybridization at a spliceosome-forming site, inhibition of transfer from the nucleus to the cytoplasm by hybridization with mRNA, translation initiation by hybridization at a translation initiation factor binding site, and the like. These antisense molecules inhibit a transcription, splicing or translation procedure to suppress expression of a target gene.

Antisense molecules used in the present invention may have any functions to suppress the expression of the target gene, and representative examples of the antisense molecules may include a triplex, a ribozyme, RNAi, or an antisense nucleic acid.

Glucosamine may be used as one preferred example of the TG2 inhibitor. The term "glucosamine" refers to a decomposition product of chitosan that is a main ingredient of the shells of crabs and shrimp. Crab or shrimp shells are composed of chitin and chitosan as main ingredients. Here, chitin is composed of 2-acetamido-2-deoxy-beta-D-glucose (N-acetylglucosamine), and chitosan is a polysaccharide formed by deacetylation of chitin, that is, poly(beta-(1,4)-glucosamine) Glucosamine has a structure represented by the following Formula 1.

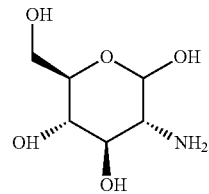

[Formula 1]

In the present invention, a glucosamine derivative may be used as the glucosamine. In the present invention, the term "glucosamine derivative" refers to a glucosamine in which a hydrogen atom of a hydroxyl group is substituted with an acyl or alkyl compound, and which has a structure represented by the following Formula 2.

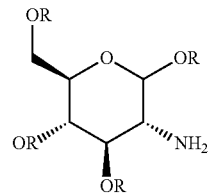

[Formula 2]

In Formula 2, R represents an acyl group having 2 to 18 carbon atoms, or a linear or branched alkyl group having 1 to 5 carbon atoms. Preferably, the residue R may be an acyl group such as an acetyl propionyl, butyryl, pentanoyl, hexanoyl, heptanoyl, octanoyl, nonanoyl, decanoyl, undecanoyl, lauryl, tridecanoyl, myristyl, pentadecanoyl, palmitoyl, margaryl, or stearyl group, or an alkyl group such as a methyl, ethyl, propyl, butyl, pentyl, isopropyl, isobutyl, or sec-butyl group.

Also, the glucosamine or a derivative thereof used in the present invention may be included in a pharmaceutical composition according to the present invention in the form of a pharmaceutically available salt according to a purpose of use. Such a form of a salt may, for example, include a sulfate of glucosamine or a derivative thereof, a hydrochloride of glucosamine or a derivative thereof, a malate of glucosamine or a derivative thereof, and the like, but the present invention is not limited thereto. The preferred form of a salt is a sulfate of glucosamine or a derivative thereof.

In the composition according to the present invention, the cyclosporine and the transglutaminase 2 inhibitor may be included at a weight ratio of 1:1.8 to 2,000, and the tacrolimus and the transglutaminase 2 inhibitor may be included at a weight ratio of 1:18 to 2,000. Also, the immunosuppressant may be administered at a higher content as a degree of severity of atopic dermatitis increases, and may be administered at a lower content as a degree of severity of atopic dermatitis decreases.

The composition according to the present invention may be formulated into oral formulations such as a powder, a granule, a tablet, a capsule, a suspension, an emulsion, a syrup, an aerosol, and the like, a sterile injectable solution, a suppository, and a preparation for percutaneous administration according to conventional methods. Carriers, excipients and diluents that may be included in the composition may include lactose, dextrose, sucrose, sorbitol, mannitol, xylitol, erythritol, maltitol, starch, acacia gum, alginate, gelatin, calcium phosphate, calcium silicate, cellulose, methyl cellulose, amorphous cellulose, polyvinyl pyrrolidone, water, methyl hydroxybenzoate, propyl hydroxybenzoate, talc, magnesium stearate, and mineral oil. The composition may be formulated using a diluent or an excipient such as a filler, an extending agent, a binding agent, a wetting agent, a disintegrating agent, a surfactant, and the like.

The composition according to the present invention may be formulated into a solid phase preparation for oral administration. The solid phase preparation for oral administration includes a tablet, a pill, a powder, a granule, a capsule, and the like. In this case, such a solid phase preparation is formulated by mixing at least one excipient, for example, starch, calcium carbonate, sucrose, lactose, or gelatin, with the active ingredient. Also, lubricants such as magnesium stearate, talc and the like maybe used in addition to the simple kinds of excipients.

Also, the composition according to the present invention may be formulated into a liquid phase preparation for oral administration. The liquid phase preparation for oral administration includes a suspension, a solution for internal use, an emulsion, a syrup, and the like. Such a liquid phase preparation encompasses various excipients, for example, a wetting agent, a sweetening agent, a flavoring agent, a preservative, and the like in addition to the inert diluents (for example, purified water, ethanol, liquid paraffin) widely used in the art.

Further, the composition of the present invention may also be formulated into a preparation for parenteral administration. The preparation for parenteral administration includes a sterilized aqueous solution, a non-aqueous solvent, a suspension, an emulsion, a lyophilized preparation, a suppository, and the like. A proper buffer solution such as a Hank's solution, a Ringer' solution, or a physiologically buffered saline may be used as the sterilized aqueous solution, and a vegetable oil such as propylene glycol, polyethylene glycol, or olive oil, or an injectable ester such as ethyl oleate may be used as the non-aqueous solvent. A preservative, a stabilizing agent, a wetting agent, an emulsifying agent, or a salt and/or buffer for control of osmotic pressure may also be used, as necessary. Meanwhile, In the case of the suppository, Witepsol, Macrogol, Tween 61, cocoa butter, laurin butter, glycerol gelatin and the like may be used as a conventional base of the suppository.

When administered to human patients, a daily used dose of the composition according to the present invention may be determined by prescription within the scope of medical judgment. The daily dose of the composition may be differently applied according to various factors including the kind and level of a reaction needed to achieve a specific therapeutically effective amount for certain patients, the optional use of another preparation, the age, weight, general health conditions and sex of a patient, the diet, an administration time, a route of administration, a secretion rate of a composition, a treatment period, and similar factors widely known in the field of medicine.

Preferably, cyclosporine may be administered at a dose of 0.025 mg/kg to 2.9 mg/kg in combination with glucosamine, and tacrolimus may be administered at a dose of 0.0025 mg/kg to 0.29 mg/kg in combination with glucosamine. As the transglutaminase 2 inhibitor, glucosamine may be prescribed and administered at a dose of 5 mg/kg to 50 mg/kg, and may be properly administered, for example, administered once to three times a day according to the skin condition of a patient. Also, cyclosporine may be administered at the maximum dose of 5 mg/kg according to a skin lesion state.

Also, the composition according to the present invention may be formulated into a solution for external use on the skin, or a cosmetic preparation. The solution for external use on the skin may include an ointment, a plaster, a spray, suspension, an emulsion, a cream, a gel, and the like.

Cyclosporine as the immunosuppressant and the transglutaminase 2 inhibitor may be included at a weight ratio of 1:1.8 to 2,000, and tacrolimus and the transglutaminase 2 inhibitor may be included at a weight ratio of 1:18 to 20,000.

According to one preferred example of the present invention, the immunosuppressant and the transglutaminase 2 inhibitor may be included at a content of 0.001 to 5% by weight, based on the total dry weight of the cosmetic composition.

In addition to the above-described active ingredients, the cosmetic composition according to the present invention may also optionally include various components widely used in the solution for external use on the skin without reducing the effects of the present invention, for example, components which can be blended with a water-soluble component, a powdery component, an oily component, a surfactant, a humectant, a viscosity controlling agent, a preservative, an antioxidant, a flavor, a pigment, and the like. Further, a humectant such as ceramide widely used as a conventional therapeutic agent for treating atopic dermatitis, a steroid such as a lipid component or hydrocortisone, a vitamin A derivative such as retinyl palmitate or/and tocopherol, other plant extracts, and the like may be prepared in the form of a liposome using known lecithin, or may be used in combination of N-stearoyl-phytosphingosine by conjugation.

A formulation of the cosmetic composition according to the present invention may be optionally selected, and prepared in various forms of conventional cosmetic formulations such as an ointment for external use on the skin, an essence, a whitening cream, a lotion, an emulsion, a pack, a general face lotion, a skin milk, a cream, a serum, a beauty soap, a toner, a medicated face lotion, a hair tonic, a body cleanser, an oily gel, and the like. The cosmetic composition according to the present invention may further include at least one additive selected from the group consisting of an oily component, water, a surfactant, a humectant, a thickener, a chelating agent, a pigment, a preservative, and a flavor. Preferred formulations include formulations of a toner, a lotion, a nourishing skin cream, a massage cream, an emollient serum, an essence, and a pack.

The cosmetic composition according to the present invention may relieve and alleviate atopic dermatitis when the cosmetic composition is applied to an inflammatory site on the skin. The amount of the cosmetic composition applied to the inflammatory site may be properly selected according to the inflammatory site of a patient, and the cosmetic composition may be typically applied once to 5 times a day.

When the composition for preventing or treating atopic dermatitis according to the present invention is used, a therapeutic effect of relieving symptoms in patients suffering from severe atopic dermatitis may be expected at the early stage. Also, since the composition may be used at a lower dose than in therapy using an immune preparation alone, the composition may be administered in combination for a long period of time, thereby alleviating pruritus and allowing atopic dermatitis patients to maintain a desirable skin condition for a long period of time. That is, when the composition for preventing or treating atopic dermatitis according to the present invention, it is possible to expect a therapeutic effect according to the relief of atopic symptoms and a prophylactic effect of preventing development of severe pruritus and dermatitis symptoms.

MODE FOR INVENTION

Hereinafter, the present invention will be described in further detail with reference to the following preferred Examples. However, it should be understood that the following Examples are given by way of illustration of the present invention only, and are not intended to limit the scope of the present invention, as apparent to those skilled in the art.

EXAMPLE 1

Determination of Therapeutic Effect on Atopic Dermatitis in Mice Suffering from Atopic Dermatitis 1.1. Experimental Materials and Methods Eight-week-old male NC/Nga mice were purchased from the Shizuoka Laboratory Animal Center (Hamamatsu, Japan). Glucosamine was purchased from Sigma-Aidrich Co. (St. Louis, Mo.), and tacrolimus (FK-506) and cyclosporine were purchased from Chong Kun Dang Pharmaceutical Corp. A Df body ointment was commercially available from Biostir Inc. (Kobe, Japan). To induce atopy in NC/Nga mice, hair was removed from the mice, and the mice's backs and ears were treated with 4% sodium dodecyl sulfate (SDS). After 3 hours, a Df body ointment was applied to the backs and ears. This procedure was repeatedly performed twice for 4 weeks. Skin lesions were determined using a clinical skin score. The clinical skin score was evaluated in levels of 0 (none) to 8 (severe), based on the symptoms of erythema/hemorrhage, scarring/dryness, edema, and excoriation/erosion. In this case, the clinical skin score was measured by summing up the levels.

The effects of an immunosuppressant and a TG2 inhibitor when administered alone and in combination were determined using the mice having a clinical skin score of 8, and the effects on alleviation of atopic dermatitis were determined using the NC/Nga mice suffering from Df-induced dermatitis.

1.2. Comparison of Effects of Immunosuppressant and TG2 Inhibitor on Alleviation of Atopic Dermatitis when Administered Alone and in Combination To determine effects by combined administration of the immunosuppressant, tacrolimus or cyclosporine, and the TG2 inhibitor, glucosamine, glucosamine was orally administered once a day for 3 weeks alone or in combination with tacrolimus or cyclosporine. As the control, PBS was administered instead of the medicine, and each group was composed of 5 mice.

1.2.1. Comparison of Clinical Skin Scores by Combined Administration of Immunosuppressant and Glucosamine Effect of Combined Administration of Tacrolimus and Glucosamine Glucosamine was administered at a dose of 500 mg/kg/day, and tacrolimus was administered at a sufficient dose of 1.0 mg/kg/day to exhibit therapeutic and prophylactic effects on atopic dermatitis. After glucosamine and tacrolimus (FK-506) were administered alone or in combination, the clinical skin scores were determined in the atopy-induced NC/Nga mice.

Figure 2:
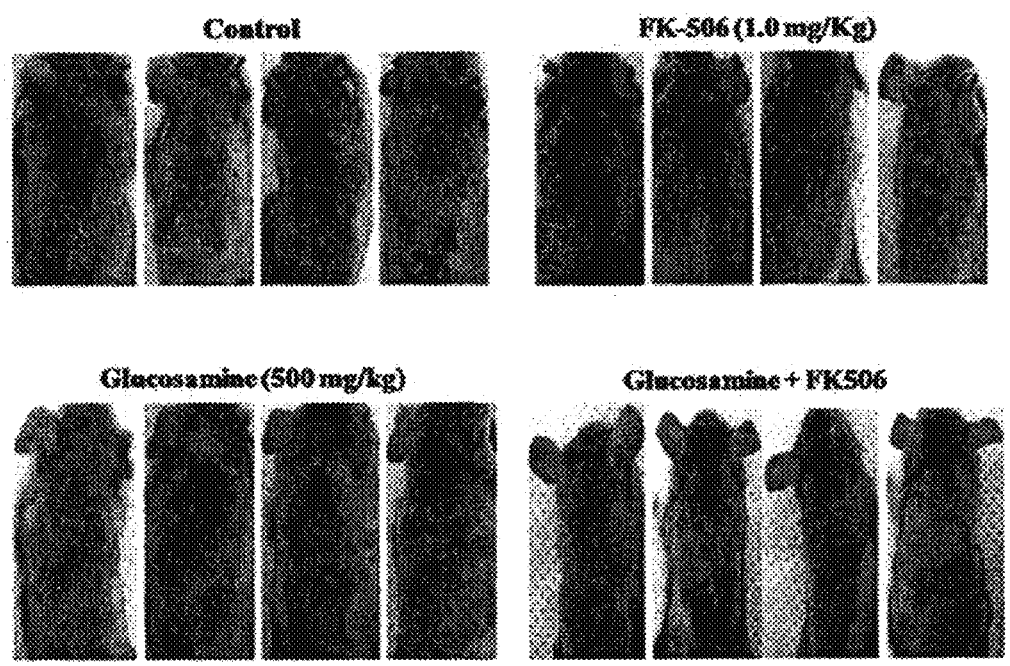
FIG. 2 is a diagram showing the results obtained by clinically determining changes in skin lesions in atopy-induced NC/Nga mice after glucosamine (500 mg/kg/day) and tacrolimus (FK-506) (1.0 mg/kg/day) are administered alone or in combination.

The results are shown in FIGS. 1 and 2.

As shown in FIGS. 1 and 2, it could be seen that the clinical skin scores were higher and lesions were more clearly alleviated in a clinical aspect in the group of mice to which tacrolimus (FK-506) was administered in combination with glucosamine, compared to the group of mice to which glucosamine or tacrolimus (FK-506) was administered alone.

Effects of Combined Administration of Cyclosporine and Glucosamine

Figure 3:
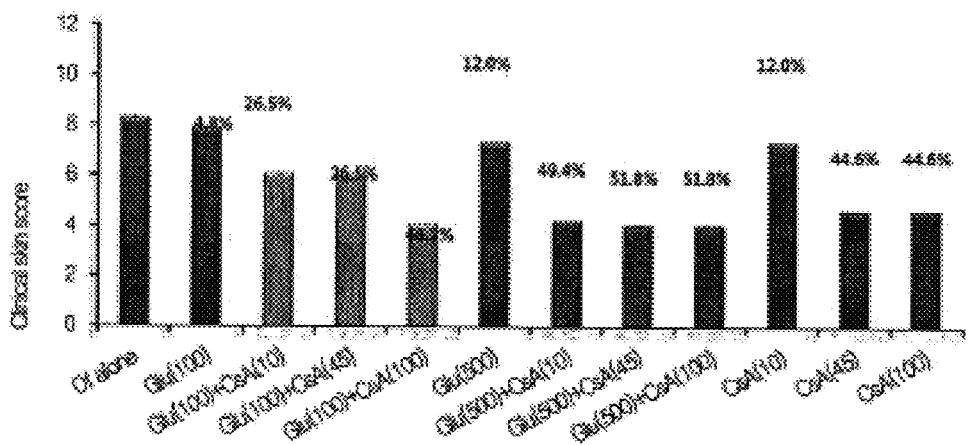
FIG. 3 is a diagram showing the results obtained by measuring and comparing clinical skin scores after cyclosporine (CsA) (10, 45, and 100 mg/kg/day) and glucosamine (100, and 500 mg/kg/day) are administered alone or in combination.

Cyclosporine (CsA) (10, 45, and 100 mg/kg/day) and glucosamine (100, and 500 mg/kg/day) were administered alone or in combination, and the therapeutic effects on the NC/Nga mice in which skin lesions were induced were determined through the clinical skin score The results are shown in FIG. 3.

As shown in FIG. 3, it could be seen that cyclosporine did not show a significant therapeutic effect when administered at a low dose of 10 mg/kg/day, but showed a significant effect when administered in combination with glucosamine (100 mg/kg/day). Also, it could be seen that glucosamine showed a similar or slightly better therapeutic effect when administered at a low dose of 500 mg/kg/day in combination with cyclosporine, compared to that of cyclosporine when administered alone at a low dose of 45 mg/kg/day and a high dose of 100 mg/kg/day.

Based on these results, it was confirmed through the clinical skin score that the composition showed a therapeutic effect when glucosamine was administered at a fixed dose of 500 mg/kg/day and cyclosporine was administered at a low dose of 2, 5, or 10 mg/kg/day.

Figure 4:
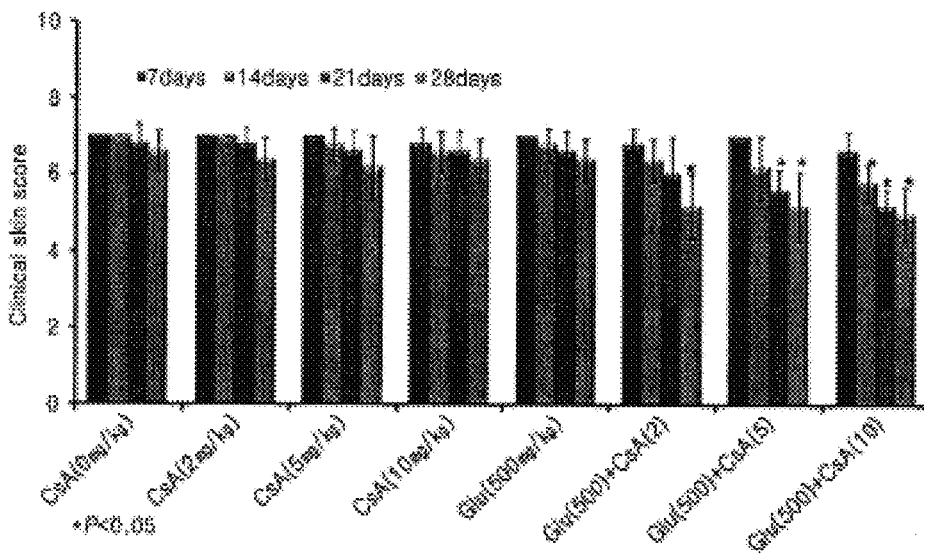
FIG. 4 is a diagram showing the results obtained by measuring and comparing clinical skin scores after glucosamine and cyclosporine (CsA) are administered alone or in combination at a fixed dose of 500 mg/kg/day and an increasing dose, respectively.
Figure 5:
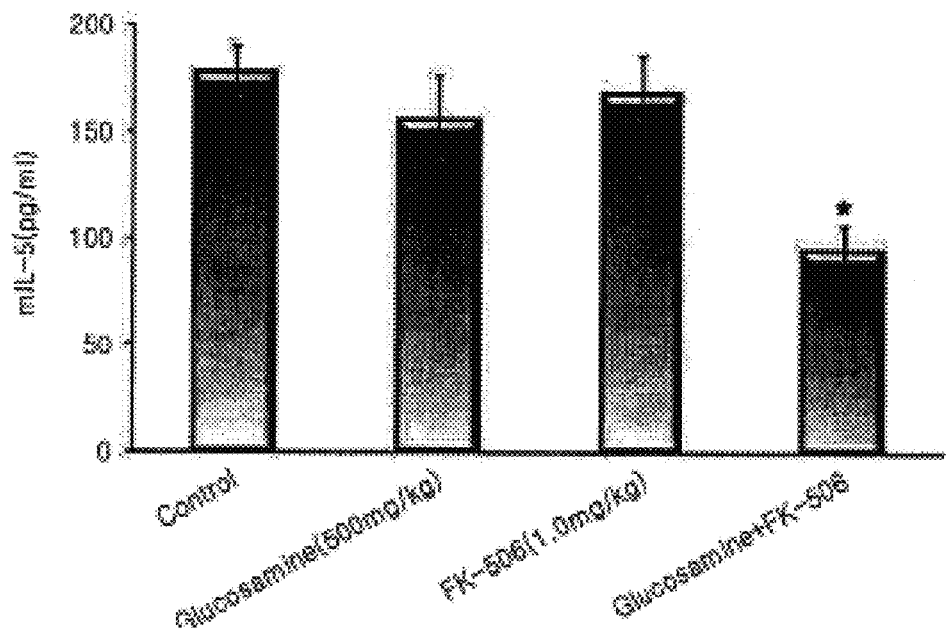
FIGS. 5 to 8 are diagrams showing the results obtained by comparing expressions of IL-5 (FIG. 5), IL-13 (FIG. 6), TARC (FIG. 7) and eotaxin (FIG. 8) after tacrolimus (FK-506) and glucosamine are administered alone or in combination at doses of 1.0 mg/kg/day and 500 mg/kg/day, respectively.
Figure 6:
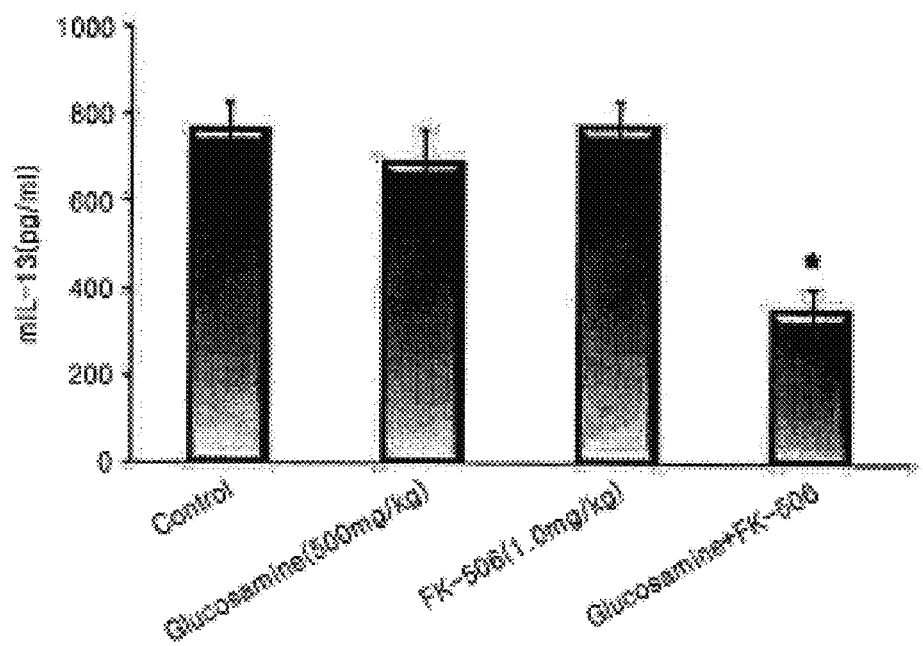
Figure 7:
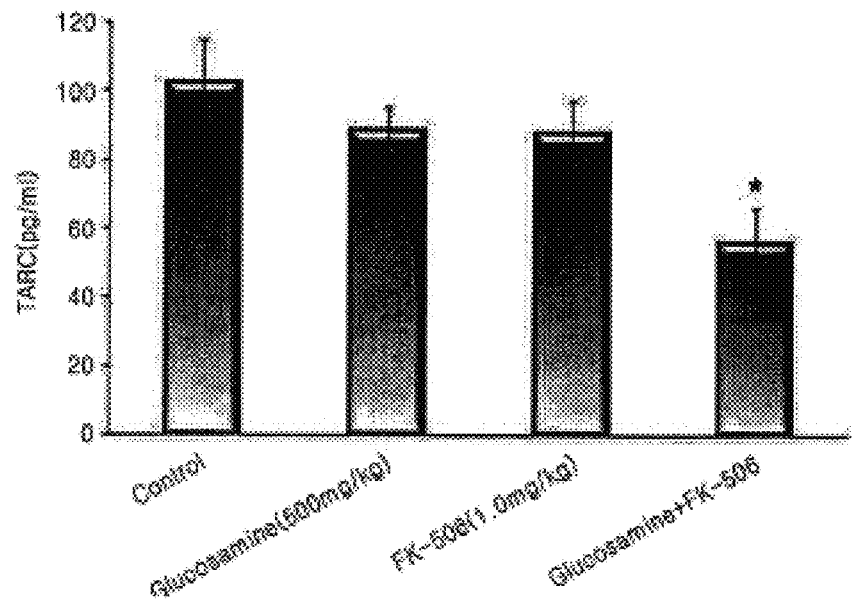
Figure 8:
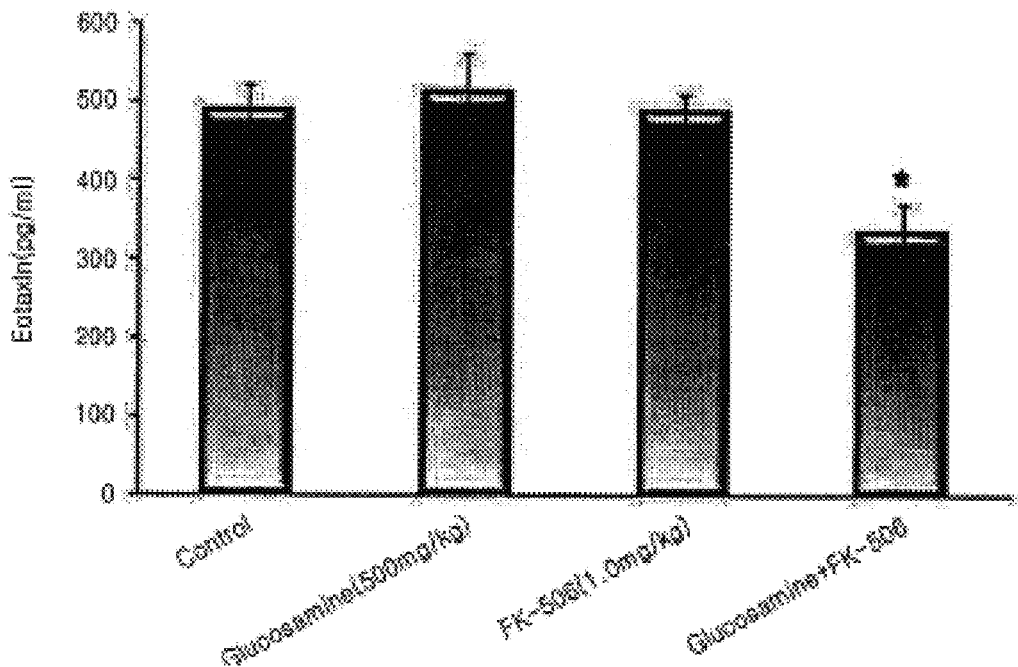

The results are shown in FIG. 4.

As shown in FIG. 4, it was revealed that the composition showed a better therapeutic effect even when cyclosporine was administered at a low dose of 2 mg/kg/day in combination with glucosamine, compared to when cyclosporine (CsA) was administered alone at a dose of 10 mg/kg/day.

1.2.2. Comparison of Secretion Levels of Cytokines and Chemokines by Combined Administration of Immunosuppressant and Glucosamine To determine a change in secretion level of cytokines and chemokines by administration of the composition including the immunosuppressant and the TG2 inhibitor, glucosamine, cells were taken from the spleen after one week had elapsed after the final administration, and cultured at a temperature of 37° C. and a 5% $CO_2$ atmosphere for 24 hours in a medium supplemented with phorbol 12-myristate 13-acetate (PMA: Sigma) and 1 µM ionomycin (Calbiochem, La Jolla, Calif., USA). The cultured supernatant was collected, and the concentrations of IL-4, IL-5, IL-13, IFN-γ, CCL17/TARC, and eotaxin were measured using an ELISA kit (R&D System, Minneapolis, Minn., USA).

Effects of Combined Administration of Tacrolimus (FK-506) and Glucosamine

Tacrolimus (FK-506) and glucosamine were administered alone or in combination at doses of 1.0 mg/kg/day and 500 mg/kg/day, respectively, and the spleen cells of the mice were analyzed through ELISA using IL-5, IL-13, eotaxin and TARC as targets.

The results are shown in FIGS. 5 to 8.

As shown in FIGS. 5 to 8, it could be seen that expression of IL-5 (FIG. 5), IL-13 (FIG. 6), TARC (FIG. 7) and eotaxin (FIG. 8) was clearly inhibited when glucosamine and tacrolimus were administered in combination, compared to when either glucosamine or tacrolimus was administered alone (p=0.008 and p=0.011) or when the control (p=0.001) was administered.

Effects of Combined Administration of Cyclosporine and Glucosamine

A low dose of cyclosporine (CsA) (2, 5, and 10 mg/kg/day) and glucosamine (500 mg/kg/day) were administered alone or in combination, and the reduction effects of IL-5, IL-13, eotaxin, TARC and TSLP in the spleen cells of the mice were compared.

The results are shown in FIG. 9.

As shown in FIG. 9, it was revealed that, when a low dose of cyclosporine and glucosamine were administered in combination, levels of the Th2 cytokines, IL-4, IL-5 and IL-13, and the chemokines, eotaxin, TARC and TSLP, were significantly reduced in all the groups treated with 2 mg/kg/day of cyclosporine (CsA), compared to the untreated group and the groups treated with cyclosporine and glucosamine alone.

1.2.3. Comparison of Immunohistochemical Changes in T Cells by Combined Administration of Immunosuppressant and Glucosamine Effects of Combined Administration of Tacrolimus (FK-506) and Glucosamine It was reported that expression of peripheral CD3+ T cells and CLA+ cells was clearly increased in children suffering atopic diseases. Effects of combined administration of the immunosuppressant, tacrolimus (FK-506), and glucosamine on invasion of Df-induced CLA+ and CD3+ T cells (indicated by green on the surface) in the NC/Nga mice were determined using an immunohistochemical method. To perform immunohistochemical analysis, immunofluorescent staining was performed on CD3+ T cells or cutaneous lymphocyte antigen (CLA). Skin samples were obtained from each mouse group, immobilized with paraffin wax, and microtomed to obtained sections having a thickness of 5 μm. Paraffin was removed and rehydrated, and the sections were heated for 5 minutes in a 100 mM citrate buffer solution (pH 6.0). The skin tissue sections were pre-cultured at room temperature for an hour in 3% bovine serum albumin (BSA), and continuously reacted overnight with an anti-CD3 antibody (dilution of 1:100: rabbit polyclonal, abcam, Cambridge, UK) or an anti-CLA antibody (rat monoclonal, Novus Biologicals, Littleton, Colo., USA) at 4° C. Then, Alexa Fluor-labeled goat anti-rabbit IgG (594; Invitrogen, Eugene, Oreg., USA) for CD3 staining, or Alexa Fluor-labeled goat anti-rat IgG and IgM (488; Invitrogen) for CLA staining was reacted at room temperature for an hour. The nuclei were stained with Hoechst 33258 (Sigma-Aldrich) as the control. The stained tissue samples were analyzed using an image analysis system (Dp Manager 1 r 2.1; Olympus Optical Co., Tokyo, Japan). Tacrolimus (FK-506) and glucosamine were administered alone or in combination at doses of 1.0 mg/kg/day and 500 mg/kg/day, respectively, and invasion of the Df-induced CLA+ and CD3+ T cells (indicated by green on the surface) in the NC/Nga mice was determined using the same method as described above.

Figure 10:
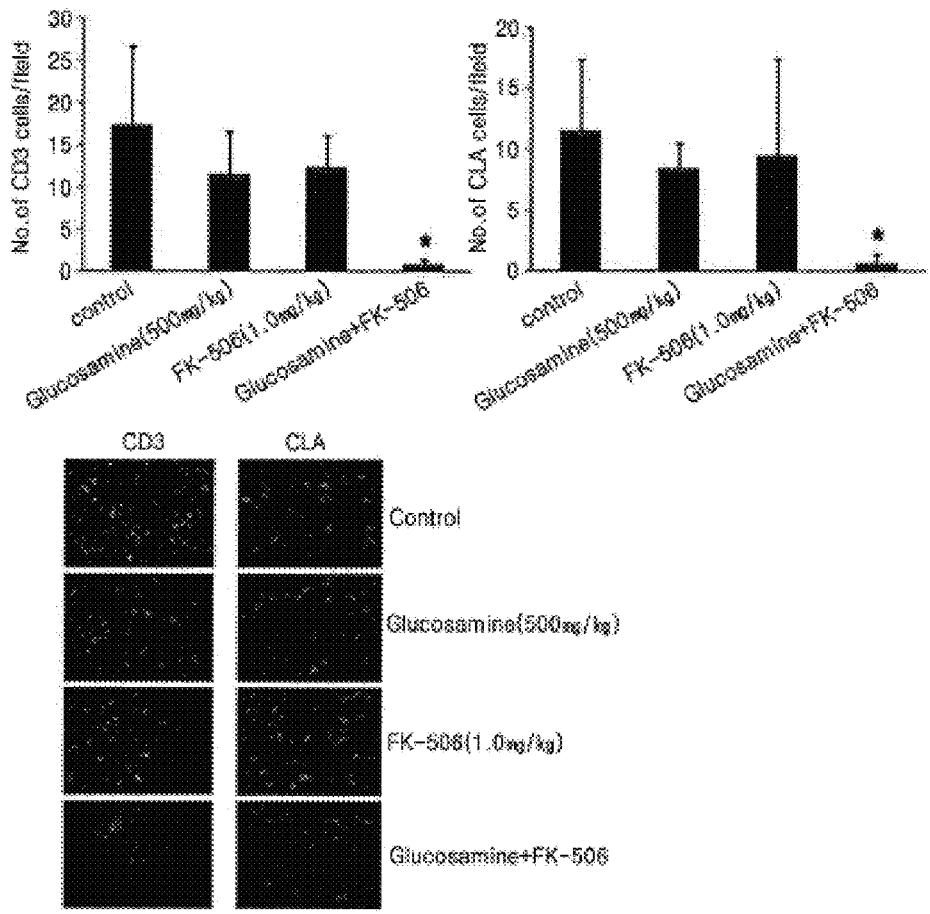
FIG. 10 is a diagram showing inhibitory effects on CLA+ and CD3+ T cells when tacrolimus (FK-506) (1.0 mg/kg/day) and glucosamine (500 mg/kg/day) are administered alone or in combination.

The results are shown in FIG. 10.

As shown in FIG. 10, it was confirmed that expression of the CLA+ and CD3+ T cells was inhibited more effectively when glucosamine and tacrolimus were administered in combination.

Effects of Combined Administration of Cyclosporine and Glucosamine

It was reported that the number and functions of regulatory T cells (Treg) regulating an immune function were small or poor in atopic dermatitis. A decrease in the number of such regulatory T cells was involved in inducing the immune imbalance in which a Th2 immune response prevailed in atopic dermatitis patients. Therefore, when cyclosporine and glucosamine were administered in combination, it was confirmed whether a change in the number of regulatory T cells was effectively caused. Single cells derived from the spleen cells were stained with FITC-anti-CD4 (GK1.5) and PE-anti-CD25 (280406) (R&D System, Minneapolis, Minn., USA). The stained cells were cultured in PBS and 2% FBS at 4° C. for 30 minutes in a dark room. The cultured cells were washed twice, and a change in the number of T cells was determined using CellQuest software (Becton Dickinson).

Figure 11:
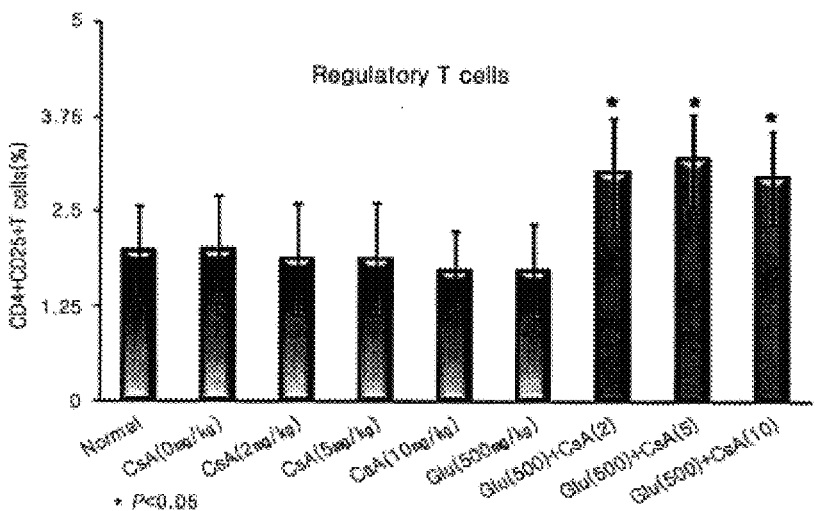
FIG. 11 is a diagram showing reduction effects on the number of CD4+CD25+ regulatory T cells when a low dose of cyclosporine (CsA) (2, 5, and 10 mg/kg/day) and glucosamine (500 mg/kg/day) are administered alone or in combination.

The results are shown in FIG. 11.

As shown in FIG. 11, it was confirmed that, when a low dose of cyclosporine (CsA) (2, 5, and 10 mg/kg/day) and glucosamine (500 mg/kg/day) were administered in combination, the number of the CD4+CD25+ regulatory T cells was significantly reduced in all the groups treated with cyclosporine (CsA) at the lowest dose of 2 mg/kg/day, compared with the untreated group (control) and the groups treated with cyclosporine and glucosamine alone.

1.2.4. Comparison of Reduction Effects of Mast Cells and Eosinocytes by Combined Administration of Immunosuppressant and Glucosamine Th2 cytokines induced growth of mast cells and eosinocytes as well as inflammation. To determine whether combined administration of an immunosuppressant and glucosamine suppressed skin infiltration of such inflammatory cells, tissues of the mice in which atopic dermatitis was induced were stained with toluidine blue or Congo red. The number of cells was observed on five high-power fields (×400) and indicated by the density of cells.

Effects of Combined Administration of Tacrolimus (FK-506) and Glucosamine

Tacrolimus (FK-506) and glucosamine were administered alone or in combination at doses of 1.0 mg/kg/day and 500 mg/kg/day, respectively, and inhibitory effects of growth and activities of mast cells and eosinocytes in the NC/Nga mice and effects on skin infiltration were compared.

Figure 12:
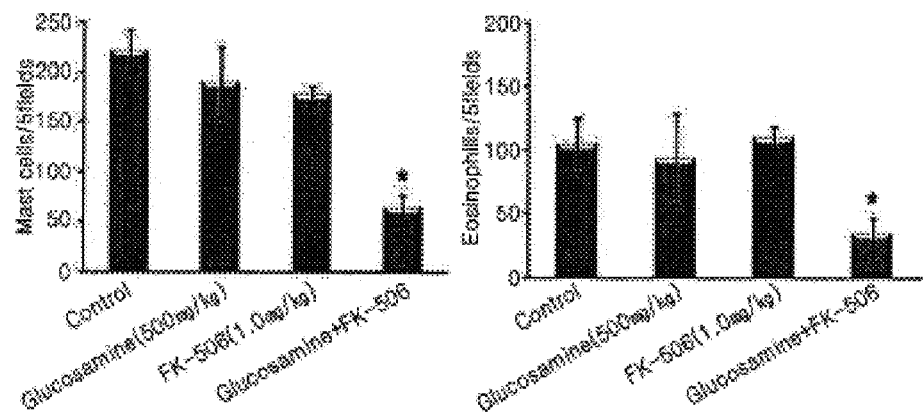
FIGS. 12 and 13 are diagrams showing inhibitory effects on growth and activities of mast cells and eosinocytes when tacrolimus (FK-506) (1.0 mg/kg/day) and glucosamine (500 mg/kg/day) are administered alone or in combination.
Figure 13:
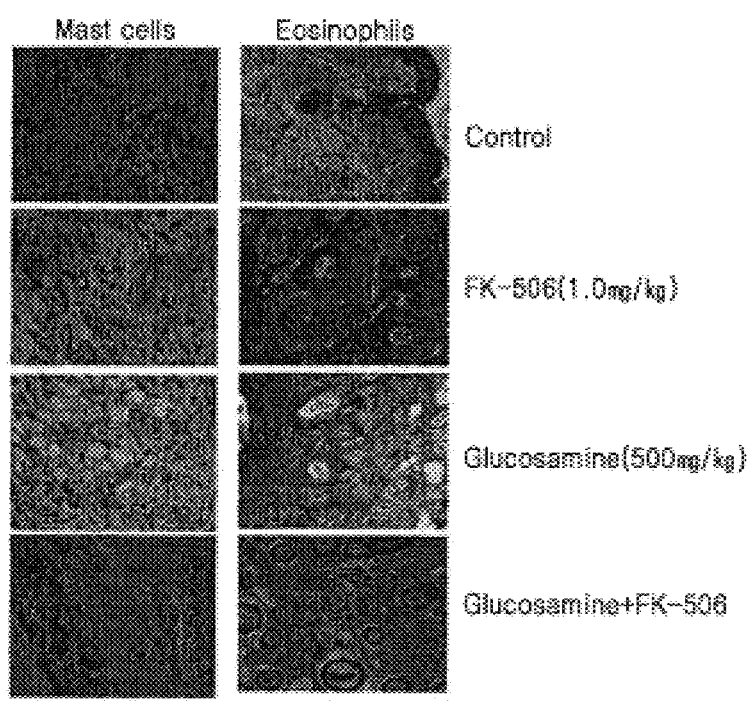

The results are shown in FIGS. 12 and 13.

As shown in FIGS. 12 and 13, it was confirmed that the number of infiltrated cells was clearly reduced when glucosamine and tacrolimus (FK-506) were administered in combination, compared to when either glucosamine or tacrolimus (FK-506) was administered alone (p=0.002 and p=0.003, control mouse P=0.001).

Effects of Combined Administration of Cyclosporine and Glucosamine

Cyclosporine and glucosamine were administered alone or in combination at a low dose of 10 mg/kg/day and a dose of 500 mg/kg/day, respectively, and the numbers of mast cells and eosinocytes infiltrated into the skin lesions were compared.

Figure 14:
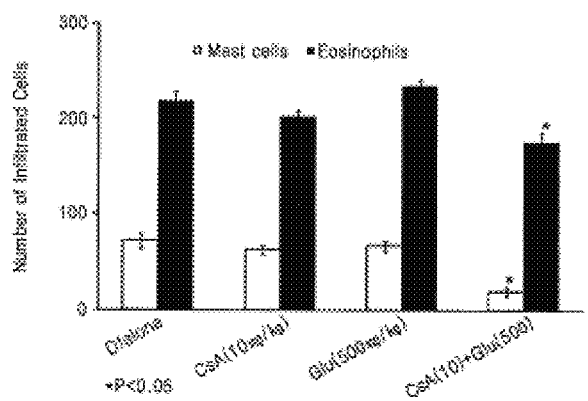
FIG. 14 is a diagram showing the results obtained by comparing the numbers of mast cells and eosinocytes penetrated into skin lesions when cyclosporine (CsA) (10 mg/kg/day) and a low dose of glucosamine (500 mg/kg/day) are administered alone or in combination.

The results are shown in FIG. 14.

As shown in FIG. 14, it was revealed that the number of mast cells and eosinocytes infiltrated into the skin lesions was significantly reduced when a low dose of cyclosporine (10 mg/kg/day) and glucosamine were administered in combination, compared to the untreated group and the groups treated with cyclosporine and glucosamine alone.

1.2.5. Reduction Effect of Serum IgE by Combined Administration of Tacrolimus (FK-506) and Glucosamine Since the major symptoms of atopic dermatitis were associated with strong Th2 immune response, IgE was produced at an excessive amount. Therefore, either glucosamine or tacrolimus was administered alone to the atopy-induced mice, or glucosamine and tacrolimus were administered in combination to measure a level of IgE in the serum. After one week had elapsed after the final administration, sera were obtained from the mice, and a total level of IgE was measured using an ELISA kit (Yamasa, Tokyo, Japan).

Figure 15:
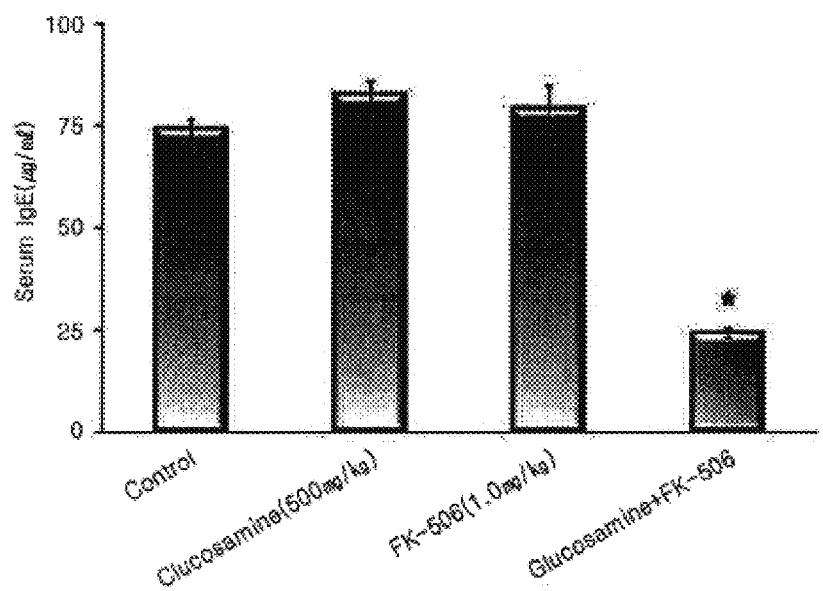
FIG. 15 is a diagram showing reduction effects of combined administration of tacrolimus (FK-506) and glucosamine on serum IgE.

The results are shown in FIG. 15.

As shown in FIG. 15, it was confirmed that the total level of IgE in the serum was more clearly reduced when either glucosamine or tacrolimus was administered alone ($p=0.002$ and $p=0.003$). Also, it was revealed that there was no clear difference in the total levels of IgE between the control and the group to which either glucosamine or tacrolimus was administered alone. Therefore, it could be seen that since a significant decrease in the level of IgE was observed when administered in combination, compared to when administered alone, the reduction effect of IgE by combined administration of tacrolimus and glucosamine was observed even when the immunosuppressant according to the present invention, tacrolimus, was used at a low dose, compared to conventional single administration.

1.2.6. Increase in Expression of Involucrin and Filaggrin by Combined Administration of Cyclosporine and Glucosamine Atopic dermatitis patients have a poor skin barrier function. Degradation of such a skin barrier function was estimated to be involved in a decrease in expression of filaggrin, and associated with involucrin forming a cornified cell envelope with proteins such as loricrin. Therefore, a change in expression of filaggrin and involucrin by combined administration of cyclosporine and glucosamine was determined. The skin cells taken from the mice were stored at −80° C. Thereafter, the cells were homogenized, and lysed in a lysis buffer (10 mM Tris-HCl containing 50 mM NaCl, 50 mM NaF, 10 mM EDTA, 1 mM DTT, 1% Triton X-100, 0.1% SDS, 1% sodium deoxycholate, 1 mM phenylmethylsulfonyl fluoride (PMSF), 5 mM leupeptin, and 10 g/ml aprotinin, pH 7.5). The same amount (20 μg) of the proteins was separated through 10% SDS polyacrylamide gel electrophoresis (SDS-PAGE), and blotted on an NC membrane. After the reaction was stopped, the reaction sample was incubated with antibodies (dilution of 1:1000) against filaggrin, involucrin and the control, β-actin (Santa Cruz, Calif., USA). The resulting reaction solution was further cultured with an HRP-bound secondary antibody (dilution of 1:3,000), blotted, and visualized using an ECL Plus™ western blotting detection reagent (Amersham, Piscataway, N.J., USA). The generated signals were determined using an image reader (LAS-3000; Fuji Photo Film, Tokyo, Japan).

Figure 16:
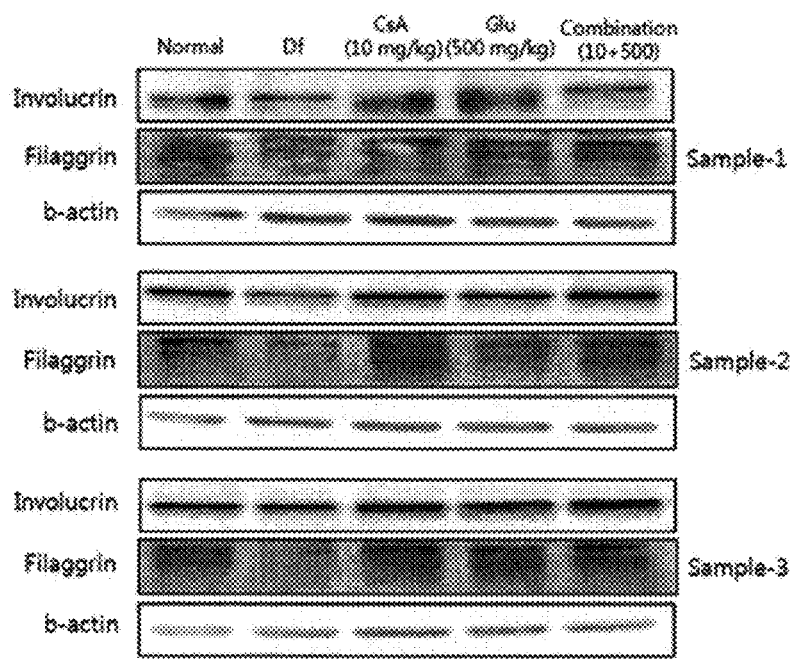
FIG. 16 is a diagram showing changes in expression of involucrin and filaggrin by combined administration of cyclosporine (CsA) and glucosamine.

The results are shown in FIG. 16.

As shown in FIG. 16, it was revealed that the involucrin and filaggrin proteins were expressed at a level similar to those of the normal groups when a low dose of cyclosporine (CsA) (10 mg/kg/day) and glucosamine (500 mg/kg/day) were administered in combination.

EXAMPLE 2

Effects of Combined Administration of Immunosuppressant and TG2 Inhibitor in Atopic Dermatitis Patients The immunosuppressant, cyclosporine, and the TG2 inhibitor, glucosamine, were administered alone or in combination to severe atopic dermatitis patients requiring administration of cyclosporine, and effects of combined administration of cyclosporine and glucosamine were determined through SCORD indexes, and determined by observing affected parts through an image and measuring an expression level of cytokines. During the experiments, the vital signs, that is, a blood pressure and a pulse, were measured after patients sat for 3 minutes to rest. According to the measurement results, it was revealed that both the blood pressures and pulses of the patients to be tested were in a normal range.

2.1. Clinical Test-SCORAD Index

Severe atopic dermatitis patients requiring administration of cyclosporine were selected as targets to be tested, and the immunosuppressant, cyclosporine, was administered alone at a given dose for 2 weeks, administered in combination with glucosamine sulfate (500 mg) for 2 weeks, administered alone for 2 weeks, and administered in combination with glucosamine sulfate for 2 weeks. Thereafter, the SCORAD indexes were measured. Cyclosporine was used at a dose of 100 mg (Cs1), 150 mg (Cs1.5) or 200 mg (Cs2), which was less than or equal to half of a dose administered. The SCORAD indexes were measured before dosage and at points of time at which the dosage methods were changed. It was assumed that an area of lesions was set to 0 to 100% according to the rule of nine, the SCORAD index was calculated as the sum (0-103) of an objective SCORAD index and a subjective SCORAD index. Here, the objective SCORAD index was calculated by dividing the severity of atopic dermatitis, which was divided into 6 categories of erythema, edema/papulation, oozing/crusts, excoriations, lichenification and skin dryness, by 0 to 3, summing up the calculated values, and adding the sum of the calculated values to ⅕ of the area of the lesions, and the subjective SCORAD index was obtained by setting each of pruritus and dyssomnia during waking hours to analog scales 0 to 10 (European Task Force on Atopic Dermatitis, 1993). However, when patients are told to evaluate subjective symptoms for pruritus and dyssomnia on a scale of 0 to 10, it is often difficult for them to do so accurately, and thus the symptoms can also be evaluated using scores from 0 to 83, including only the objective SCORAD index rather than the subjective measures (Kunz, et al., Dermatology 1997; 195:10-19). Therefore, only the objective SCORAD index was evaluated in this Example.

Figure 17:
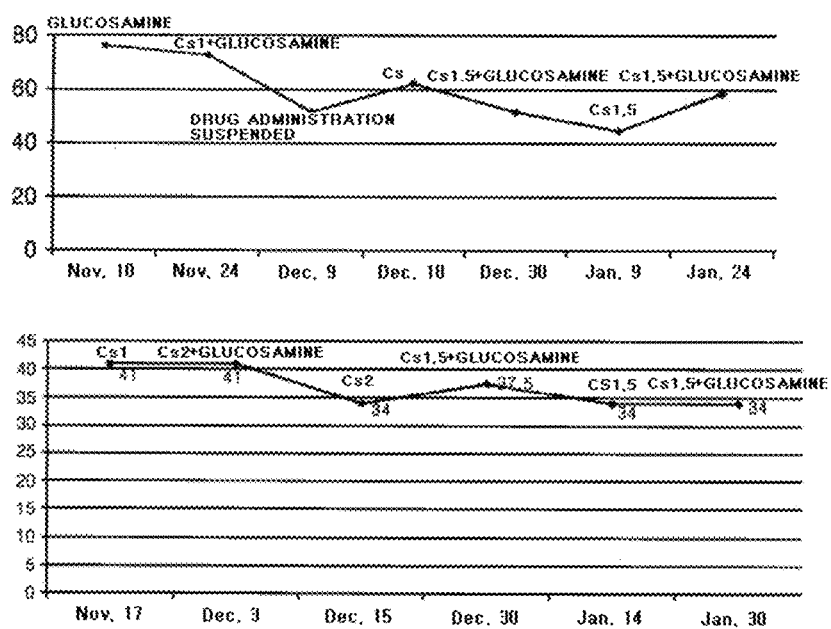
FIG. 17 is a diagram showing SCORAD indexes measured whenever dosage methods are changed by repeatedly performing a method of administering glucosamine to atopic dermatitis patients alone and a method of administering a composition including a combination of cyclosporine and glucosamine.

The results are shown in FIG. 17.

As shown in FIG. 17, there was no change in SCORAD indexes in a period of time (November 10 to November 24) in which glucosamine was administered alone to the atopic dermatitis patients. However, as soon as cyclosporine and glucosamine were administered in combination, there was a sudden decrease in SCORAD indexes from 72.5 to 51.5. The SCORAD indexes which had increased after discontinuance of the drug (December 9) decreased under single administration of cyclosporine (December 18) and subsequent combined administration (December 30). Thereafter, it was confirmed that, as soon as cyclosporine was administered again (January 9), the SCORAD indexes which had decreased under the previous treatment SCORAD increased. In another group of patients, there was hardly a change in SCORAD indexes during an administration period (November 17 to December 1) in which cyclosporine was administered alone. Such results supported the previous reports disclosing that some individual patients were resistant to cyclosporine. The SCORAD index drastically decreased from 41 to 34 during an administration period (December 1 to December 15) in which cyclosporine and glucosamine were administered in combination. When cyclosporine was re-administered alone (December 15), the SCORAD index increased, and then decreased under the combined administration (December 30). That is, single administration of glucosamine resulted in a poor therapeutic effect, and single administration of cyclosporine caused an increase in SCORAD indexes, that is, a decrease in therapeutic effect, in some cases. On the other hand, combined administration of cyclosporine and glucosamine resulted in an excellent therapeutic effect, compared to that of the single administration of glucosamine or cyclosporine. Also, the dose of cyclosporine upon combined administration was typically a half of the dose of cyclosporine used.

2.2. Measurement of SCORAD Indexes in 10 Atopic Dermatitis Patients According to Combined Administration of Cyclosporine and Glucosamine To determine a therapeutic effect of combined administration of cyclosporine and glucosamine on atopic dermatitis in more patients over an extended period of time, 10 atopic dermatitis patients were selected as targets to be tested, and measured for SCORAD index. Like the above-described method, single administration of cyclosporine and combined administration of cyclosporine and glucosamine were repeatedly performed at intervals of 2 weeks, and changes in SCORAD indexes were observed for 20 weeks. The amount of cyclosporine used was 2 to 2.9 mg/kg/day (average: 2.4 mg/kg/day), and the amounts of glucosamine were 1,000 mg/day in the case of adults, and 500 mg/day in the case of young children. The changes in the SCORAD indexes of the 10 patients were plotted on one graph. In this case, the changes in SCORAD indexes of a group of 5 patients (SEQ1) in which combined administration of glucosamine and cyclosporine was performed first, and the changes in SCORAD indexes of a group of 5 patients in which single administration of cyclosporine was performed first were determined.

Figure 18:
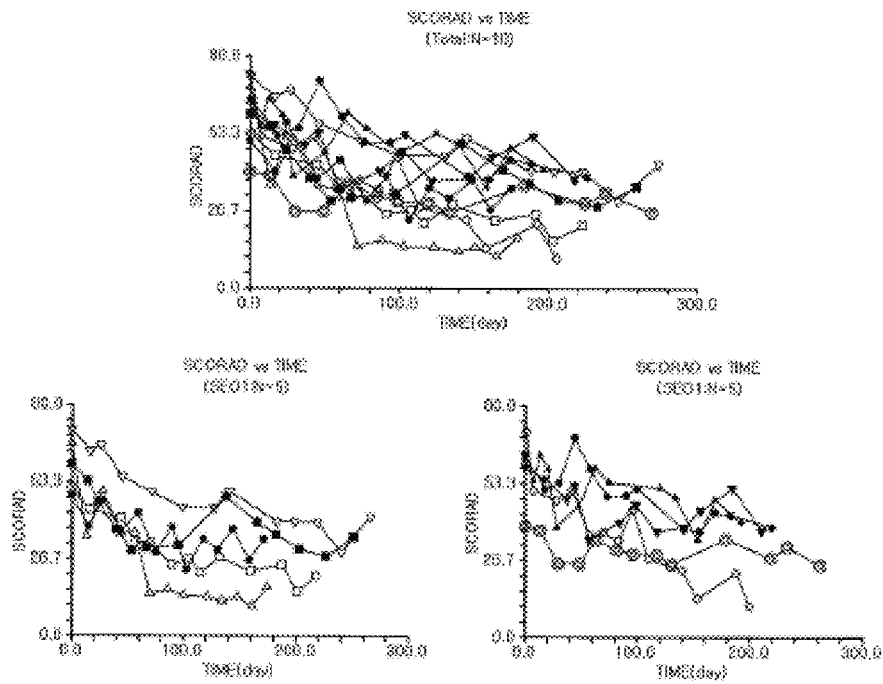
FIG. 18 is a diagram showing SCORAD indexes measured whenever dosage methods are changed while alternately performing single-combined administration and combined-single administration (upper panel: results obtained from a total of 10 patients, lower left panel: results obtained from a total of 5 patients when combined administration is performed first, and lower right panel: results obtained from a total of 5 patients when combined administration is performed later).

The results are shown in FIG. 18.

As shown in FIG. 18, it could be seen that the SCORAD index decreased to 38.4 when cyclosporine and glucosamine were administered in combination to the patients whose SCORAD index was 50.4 at the beginning, increased to 48.4 when only cyclosporine was administered again, and decreased again to 37.4 when the combined administration was performed. In another group of patients, the SCORAD index was 68.4 at the beginning, but suddenly decreased to 35.5 within 2 weeks when cyclosporine and glucosamine were administered in combination. That is, it was confirmed that the therapeutic effect was poor upon single administration of cyclosporine, and the atopic symptoms were aggravated again when cyclosporine was administered alone in the patients whose atopic symptoms were relieved by combined administration of cyclosporine and glucosamine. On the other hand, when cyclosporine and glucosamine were administered in combination, cyclosporine and glucosamine were used at doses less than or equal to a half of the sum of cyclosporine and glucosamine when glucosamine or cyclosporine was administered alone, but the therapeutic effect on atopic dermatitis was excellent. From these results, it could be seen that a combination of the two compounds caused a synergic effect in treating atopic dermatitis.

Figure 19:
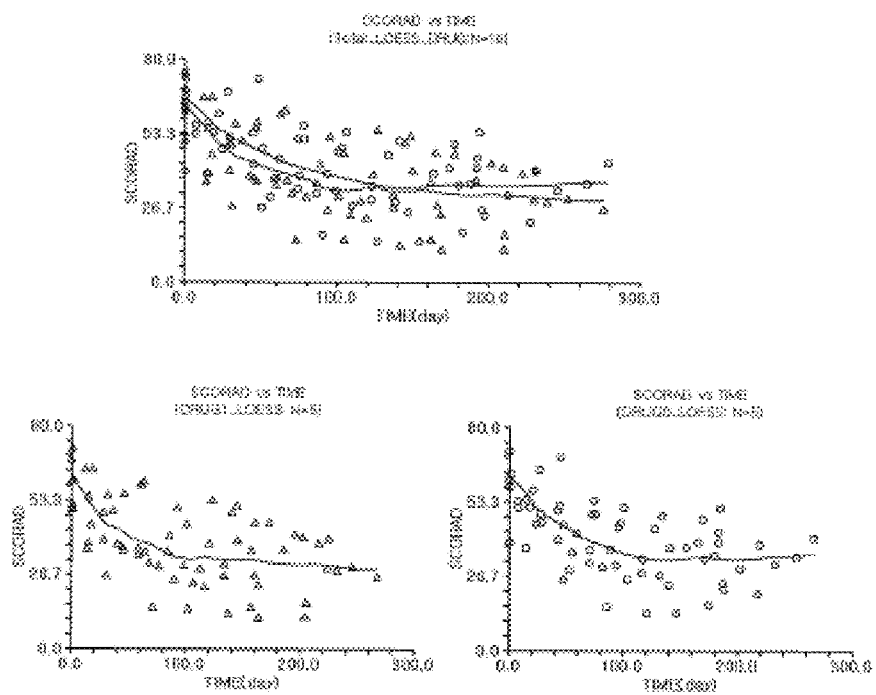
FIG. 19 is a diagram showing an average change in SCORAD indexes obtained for 5 patients when combined administration is performed first (lower left panel); an average change in SCORAD indexes obtained for 5 patients when single administration is performed first (lower right panel); and comparison of average lines plotted from the results of a total of 10 patients (upper panel) after calculation of average values of SCORAD indexes shown in FIG. 18.

An average value of the SCORAD indexes of the 10 atopic dermatitis patients was calculated, and an average change in SCORAD indexes of the 5 patients (DRUG1) in which the combined administration was performed first, and an average change in SCORAD indexes of the 5 patients (DRUG0) in which the single administration was performed first were determined. Then, average lines plotted from the results of all the patients were drawn, and compared. The results are shown in FIG. 19.

Since it is known that atopic symptoms recur when cyclosporine is discontinued, in consideration of aggravation of the atopic symptoms that may occur when the immunosuppressant is suddenly discontinued in the patients suffering severe atopic symptoms, in the clinical tests performed on 10 patients, cyclosporine and glucosamine were administered with no wash-out period (a time waiting without administering a drug of interest until the drug is removed from the body) between administrations of the drugs while repeatedly performing single administration followed by combined administration, or combined administration followed by single administration. Therefore, since the half-life of glucosamine in the body is one day, when the drug was administered, the results were corrected for two parameters of glucosamine and time, in consideration of the gradual increase of concentration of the drug in the blood over 3 days and the slow decrease over 3 days after discontinuance of the drug. The objective functional values (OFV) obtained when cyclosporine and glucosamine were administered in combination and when cyclosporine was administered alone were calculated based on the corrected results.

Figure 20:
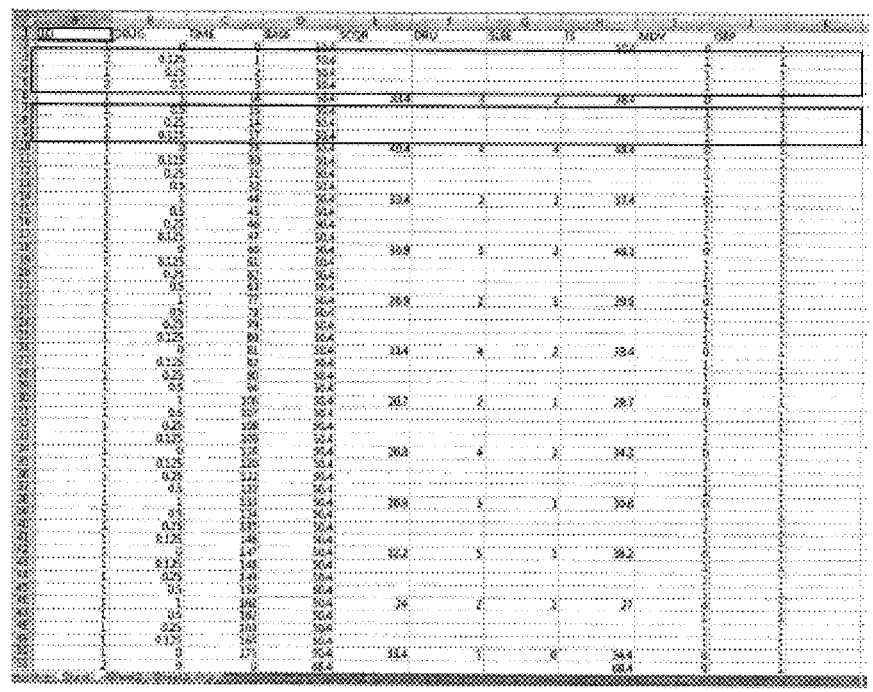
FIG. 20 is a diagram showing the results obtained by calculating objective functional values (OFV) when glucosamine is administered in combination with cyclosporine and when cyclosporine is administered alone.

The results are shown in FIG. 20.

As shown in FIG. 20, it was revealed that the objective functional values 631.640 and 653.153 were obtained by combined administration and single administration, respectively. When a difference in objective functional values in two parameters was greater than 5.99, a p-value was less than 0.05. In this case, since a difference in the objective functional values obtained by combined administration and single administration was approximately 21.5, this value satisfied p-value<0.05, indicating that the synergic effect appeared when cyclosporine was administered in combination with glucosamine, compared to when cyclosporine was administered alone.

2.3. Change in Lesions in Atopic Dermatitis Patients According to Combined Administration of Cyclosporine and Glucosamine A graduated ruler was placed at a distance of 30 cm to the side of an affected part, and images were taken at intervals of 4 weeks. A corresponding medical resident professionally took pictures of images, and was trained to standardize the images. Images of the lesion were obtained at a constant posture and distance, and the intensity of illumination in a shooting place was maintained constantly. The images were always taken at the same posture, and thus the changes in lesions before and after administration were easily compared.

Figure 21:
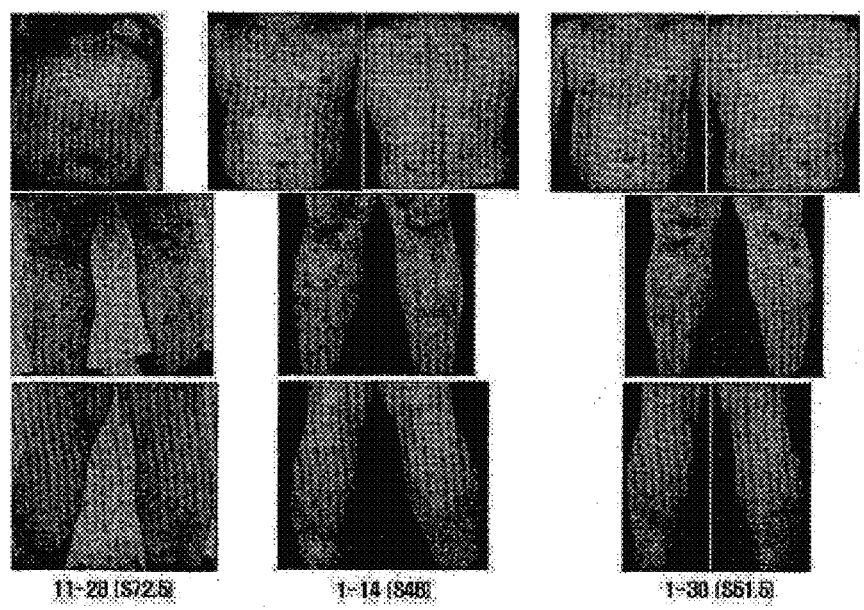
FIG. 21 is a diagram showing the results obtained by imaging affected parts at given points of time after combined administration of cyclosporine and glucosamine.

The results are shown in FIG. 21.

As shown in FIG. 21, before the combination therapy, erythema and edema on lesions were severe, patients complained of pains due to especially pervasive erythema and edema on both pelvic limbs, and excoriations due to pruritus were clearly observed. After the combination therapy was repeatedly performed twice, it was confirmed from the images that a large portion of the lesions disappeared, and the excoriations were significantly reduced as well as the erythema and edema in each lesion. Also, it could be seen that the lesions were slightly aggravated after a change of dosage methods from combined administration of cyclosporine and glucosamine to single administration of cyclosporine, and thus the erythema recurred in some skin parts and the excoriations were also slightly aggravated.

2.4. Analysis of Expression Level of Cytokine According to a Change of Dosage Methods Blood was drawn before drug administration and at points of time at which the dosage methods were changed, that is, every two weeks, to measure the concentrations of cytokines IL-4, IL-5, IFN-β, and IFN-γ using a known RT-PCR method.

Figure 22:
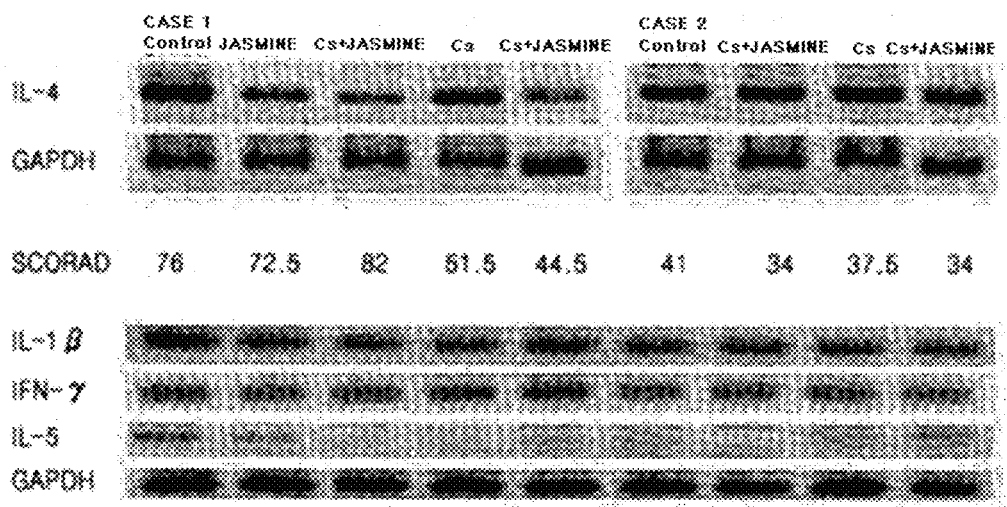
FIG. 22 is a diagram showing the results obtained by analyzing expression levels of cytokines (i.e., IL-4, IL-5, IFN-β, and IFN-γ) after combined administration of cyclosporine and glucosamine (jasmine).
Figure 23:
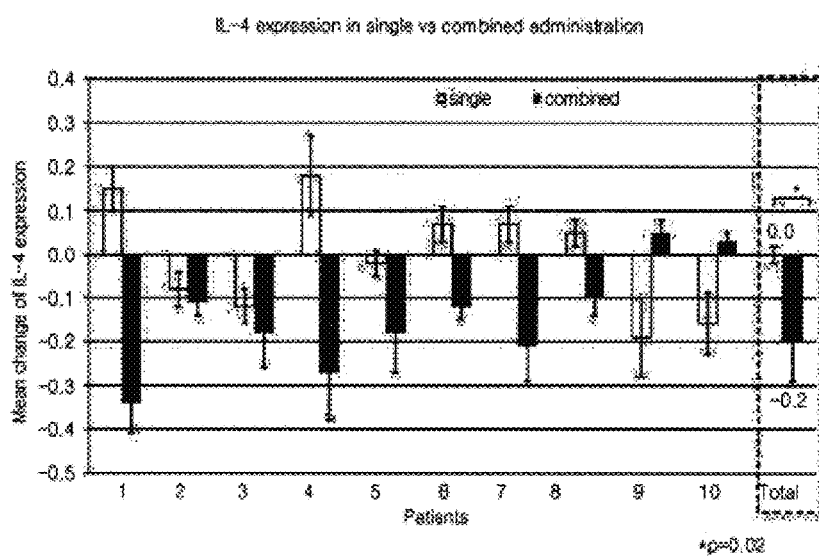
FIG. 23 is a diagram showing average values of changes in IL-4 expression levels when cyclosporine is administered alone and when cyclosporine and glucosamine are administered in combination.

The results are shown in FIGS. 22 and 23.

As shown in FIG. 22, it was revealed that, when glucosamine and cyclosporine were administered in combination, the levels of the cytokines IL-4, IL-5, IFN-β, and IFN-γ were reduced. In particular, it was revealed that an expression level of IL-4 was significantly reduced by the combined administration, and an expression level of IL-5 was also drastically reduced in the case of Patient 1. As shown in FIG. 23, the averages of changes in IL-4 expression levels were plotted on the graphs when glucosamine and cyclosporine were administered in combination and when cyclosporine was administered alone. As a result, it was also confirmed that there was a significant difference in the change in IL-4 expression levels when glucosamine and cyclosporine were administered in combination.

EXAMPLE 3

Calculation of Proper Dosage Concentration for Humans

To determine a combined dose of the immunosuppressant and the transglutaminase 2 inhibitor for humans when administered in combination, cell experiments and animal experiments were performed to calculate a proper dose in humans.

The minimum and maximum doses of cyclosporine and glucosamine obtained through the experiments conducted at a cell level are listed in the following Table 1.

TABLE 1

|  | Cyclosporine | Glucosamine |
| --- | --- | --- |
| Minimum dose | 1 ng/ml | 0.01 to 0.1 mM |
| Maximum dose | 100 ng/ml | 1 to 5 mM |

Since tacrolimus was required at a lower dose than cyclosporine by a factor of 10, tacrolimus was administered at doses of 0.1 ng/ml and 10 ng/ml when glucosamine was administered at the minimum and maximum doses, respectively. Therefore, it was confirmed that there was no difference in inhibition level even when cyclosporine was administered at a dose which was 10 times that of tacrolimus.

To convert the values obtained through the experiments conducted at a cell level into a dose directly administered to animals, the dose of the drug was converted based on the assumption that the weight of the animal was approximately 20 g. Since 1 mM glucosamine corresponded to a dose of glucosamine which was administered at 10 mg/head, a value of 0.1 mM was converted into 1 mg/head. In this case, it was confirmed that glucosamine and cyclosporine were effective against atopy diseases when glucosamine and cyclosporine were administered at doses of 10 mg and 200 ng, respectively. Based on these results, the minimum and maximum doses of cyclosporine and glucosamine in an animal experiment model were converted as follows. The dose of tacrolimus was converted into 1/10 of the following value.

TABLE 2

|  | Cyclosporine | Glucosamine | Cyclosporine (dose per kg) | Glucosamine (dose per kg) |
| --- | --- | --- | --- | --- |
| Minimum dose | 0.5 to 1 μg | 0.1 to 1 mg | 0.025 to 0.05 mg/kg | 5 to 50 mg/kg |
| Maximum dose | 50 to 100 μg | 10 to 20 mg | 2.5 to 5 mg/kg | 500 to 1,000 mg/kg |

The minimum/maximum doses used in the animals were converted into a proper dose for use in humans. In general, there was no significant difference in blood glucosamine concentrations between the animals and humans. It was revealed that the blood concentration was doubled in the case of humans when glucosamine was administered at a dose of 1,500 mg/day, compared to when glucosamine was administered at a dose of 750 mg/day, and an increase in the blood concentration was not proportional to the dose when administered at a dose greater than 1500 mg/day, and thus there was no clear difference in the blood concentrations with a decrease in concentration of glucosamine. When cyclosporine was administered at a dose of 3 mg/kg, the average blood cyclosporine concentration was measured to be 94.2 ng/ml (22.1 to 156.2 ng/ml). The final minimum/maximum doses of cyclosporine and glucosamine when administered in combination are listed in the following Table 3.

TABLE 3

|  | Cyclosporine | Glucosamine |  |
| --- | --- | --- | --- |
| Minimum dose | 0.025 to 0.05 mg/kg | 5 to 50 mg/kg |  |
| Maximum dose | 2.5 to 5 mg/kg | 500 to 1,000 mg/kg | Less than 3 mg/kg in the case of cyclosporine when administered at low dose |

Therefore, it was confirmed that combined dosage of cyclosporine and glucosamine which were able to be finally administered to humans was in a range of a minimum of cyclosporine 0.025 mg/kg/day+glucosamine 5 mg/kg/day and a maximum of cyclosporine 2.9 mg/kg/day+glucosamine 50 mg/kg/day.

A proper dose which could be administered to humans was examined through the dosage values as described above. As a result, it was revealed that glucosamine was generally administered at a dose of 12 to 17 mg/kg, and cyclosporine was generally administered at a dose of 1 to 2.9 mg/kg, indicating that the most proper ratio of glucosamine and cyclosporine was in a range of 5 to 30:1 in order to exhibit an effect of treating and preventing atopic dermatitis.

Also, since tacrolimus is required at a higher dose than cyclosporine, it was judged that the most proper content ratio at which to administer glucosamine and tacrolimus in combination was 25 to 300:1.

Further, immunosuppressive effects according to the kinds of immunosuppressants were further confirmed through experiments conducted to determine a proper dosage concentration.

Figure 24:
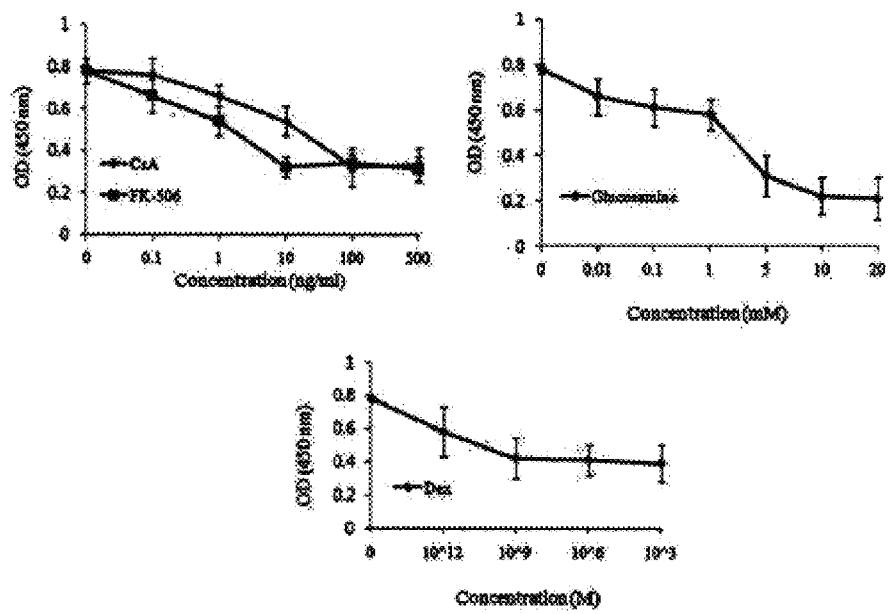
FIGS. 24 to 26 are diagrams showing the results determining inhibitory effects on inflammation when immunosuppressants, tacrolimus (FK-506), cyclosporine, glucosamine, and dexamethasone, are administered alone through changes in concentrations of IFN-g (FIG. 24), IL-4 (FIG. 25), and IL-5 (FIG. 26).
Figure 25:
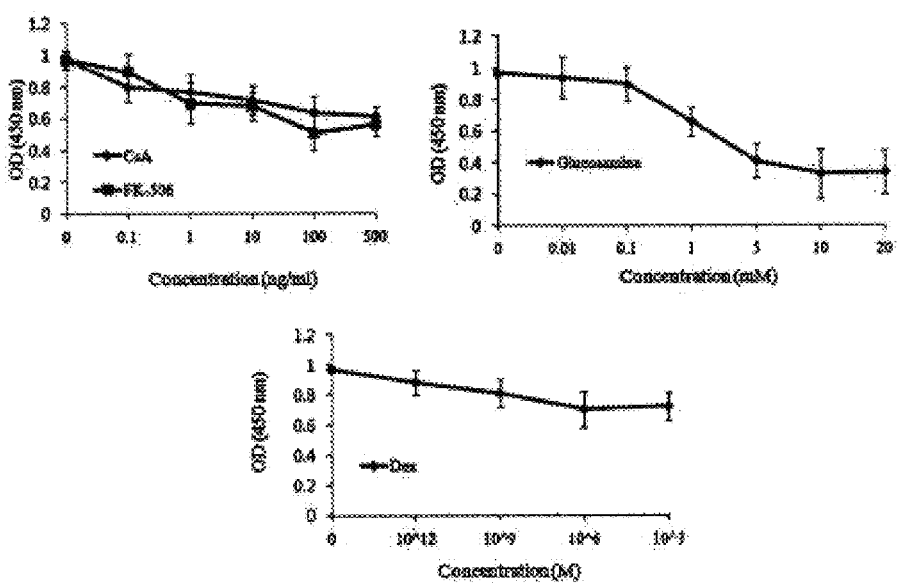
Figure 26:
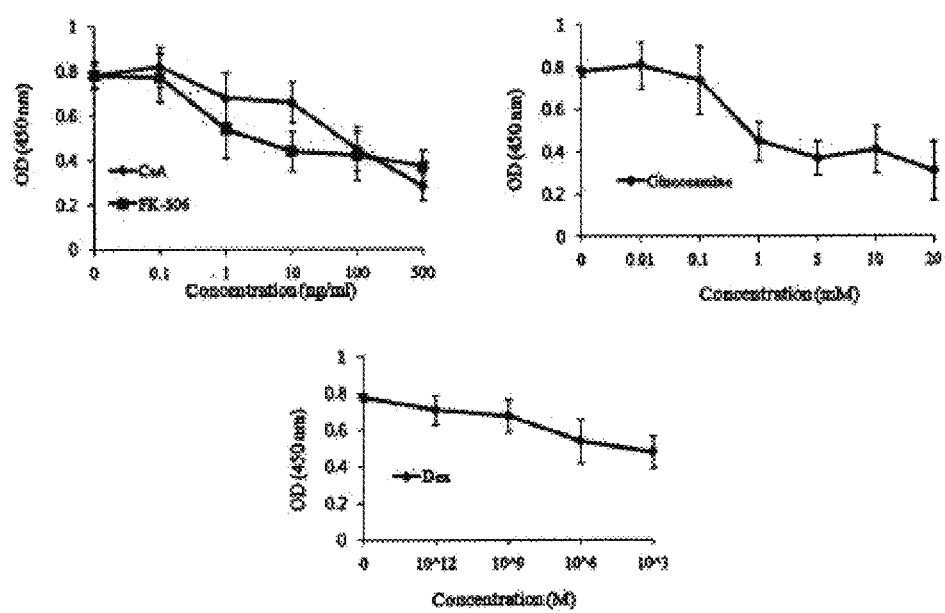

The results are shown in FIGS. 24 to 26.

As shown in FIGS. 24 to 26, it could be seen that cyclosporine, tacrolimus (FK-506), and dexamethasone showed similar patterns and suppressed an immune response. Therefore, dexamethasone was also expected to have similar effects to one of the immunosuppressants for the purpose of preventing or treating atopic dermatitis when administered in combination with glucosamine according to the present invention. Also, it was noted that pimecrolimus, which is known to be highly similar to tacrolimus, was usable as the immunosuppressant for combined administration according to the present invention.

PREPARATIVE EXAMPLE 1

Pharmaceutical Preparation 1.1. Preparation of Powder

| | |
|---|---|
| Immunosuppressant and transglutaminase 2 inhibitor | 2 g |
| Lactose | 1 g |

The components were mixed, and filled in an airtight pack to prepare a powder.

1.2. Preparation of Tablet

| | |
|---|---|
| Immunosuppressant and transglutaminase 2 inhibitor | 100 mg |
| Corn starch | 100 mg |
| Lactose | 100 mg |
| Magnesium stearate | 2 mg |

The components were mixed, and tablet-pressed to prepare a tablet according to a conventional method of preparing a tablet.

1.3. Preparation of Capsule

| | |
|---|---|
| Immunosuppressant and transglutaminase 2 inhibitor | 100 mg |
| Corn starch | 100 mg |
| Lactose | 100 mg |
| Magnesium stearate | 2 mg |

The components were mixed, and filled in a gelatin capsule to prepare a capsule according to a conventional method of preparing a capsule.

1.4. Preparation of Injection

| | |
|---|---|
| Immunosuppressant and transglutaminase 2 inhibitor | 100 mg |
| Mannitol | 180 mg |
| $Na_2HPO_4 \cdot 12H_2O$ | 26 mg |
| Distilled water | 2,974 mg |

The components were mixed, and an injection was prepared according to a conventional method.

PREPARATIVE EXAMPLE 2

Cosmetic Preparation 2.1. Preparation of Toner (Skin Lotion)

| | |
|---|---|
| Immunosuppressant and transglutaminase 2 inhibitor | 0.5% |
| Beta-1,3-glucanase | 1.0% |
| Butylene glycol | 2.0% |
| Propylene glycol | 2.0% |
| Carboxyvinyl polymer | 0.1% |
| Peg-12 nonylphenyl ether | 0.2% |
| Polysorbate 80 | 0.4% |
| Ethanol | 10.0% |
| Triethanolamine | 0.1% |
| Preservative, pigment, flavor | proper amounts |
| Purified water | to 100% |

2.2. Preparation of Lotion (Milk Lotion)

| | |
|---|---|
| Immunosuppressant and transglutaminase 2 inhibitor | 0.5% |
| Beta-1,3-glucanase | 1.0% |
| Wax | 4.0% |
| Polysorbate 60 | 1.5% |
| Sorbitan sesquioleate | 1.5% |
| Liquid paraffin | 0.5% |
| Caprylic/capric triglyceride | 5.0% |
| Glycerine | 3.0% |
| Butylene glycol | 3.0% |
| Propylene glycol | 3.0% |
| Carboxyvinyl polymer | 0.1% |
| Triethanolamine | 0.2% |
| Preservative, pigment, flavor | proper amounts |
| Purified water | to 100% |

2.3. Preparation of Nourishing Skin Cream

| | |
|---|---|
| Immunosuppressant and transglutaminase 2 inhibitor | 1.0% |
| Beta-1,3-glucanase | 5.0% |
| Wax | 10.0% |
| Polysorbate60 | 1.5% |
| Peg 60 hydrogenated castor oil | 2.0% |
| Sorbitan sesquioleate | 0.5% |
| Liquid paraffin | 10.0% |
| Squalane | 5.0% |
| Caprylic/capric triglyceride | 5.0% |
| Glycerine | 5.0% |
| Butylene glycol | 3.0% |
| Propylene glycol | 3.0% |
| Triethanolamine | 0.2% |
| Preservative, pigment, flavor | proper amounts |
| Purified water | to 100% |

The invention claimed is:

1. A method for treating atopic dermatitis in a subject comprising administering to the subject a pharmaceutical composition comprising an immunosuppressant and a transglutaminase 2 inhibitor as active ingredients,
wherein the immunosuppressant is cyclosporine or tacrolimus, and the transglutaminase 2 inhibitor is glucosamine,
wherein when the immunosuppressant is cyclosporine, the cyclosporine and the glucosamine are included in a weight ratio of 1:10 to 1:500, and
wherein when the immunosuppressant is tacrolimus, the tacrolimus and the glucosamine are included in a weight ratio of 1:18 to 1:1,000.

* * * * *